United States Patent [19]

Konotchick

[11] Patent Number: 5,267,938
[45] Date of Patent: Dec. 7, 1993

[54] MAGNETIC STIMULATION DEVICE

[76] Inventor: John A. Konotchick, 3116 Mercer La., San Diego, Calif. 92122

[21] Appl. No.: 720,198

[22] Filed: Jun. 24, 1991

[51] Int. Cl.⁵ ............................................. A61B 17/52
[52] U.S. Cl. .................................................... 600/9
[58] Field of Search ..................................... 600/9–15

[56] References Cited

U.S. PATENT DOCUMENTS

| | | | |
|---|---|---|---|
| 4,994,015 | 2/1991 | Cadwell | 600/13 |
| 5,061,234 | 10/1991 | Chaney | 600/14 |
| 5,066,272 | 11/1991 | Eaton et al. | 600/14 |

Primary Examiner—Lee S. Cohen
Assistant Examiner—John P. Lacyk
Attorney, Agent, or Firm—John R. Ross

[57] ABSTRACT

A magnetic stimulator device for inducing electrical pulses in human or animal nerve tissue. A high power electrical current source provides specially defined current pulses to a magnetic coil which produces non-uniform magnetic fields which are concentrated at a location near one position on the coil and reduced at locations near other positions on the coil. In a preferred embodiment of the present invention a variable resistance switch is used to control the shape of the induced pulses.

22 Claims, 8 Drawing Sheets

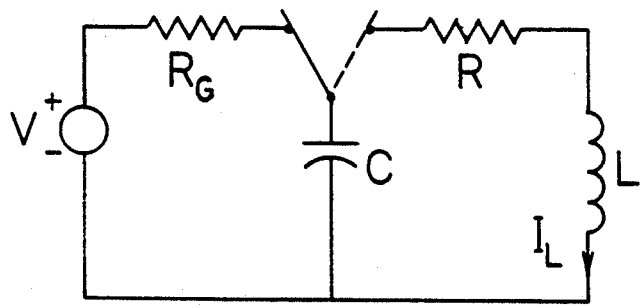
PRIOR ART
FIG. 1
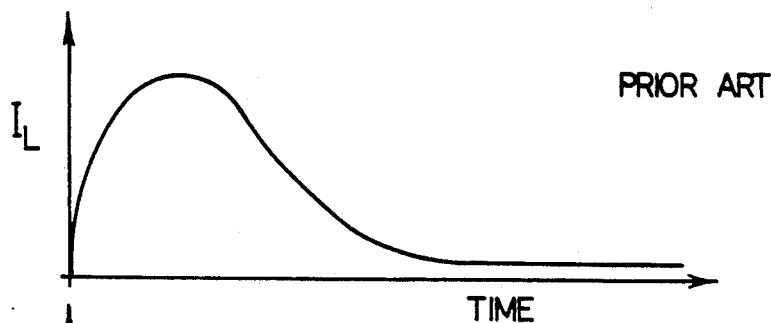
PRIOR ART
FIG. 2A
FIG. 2B
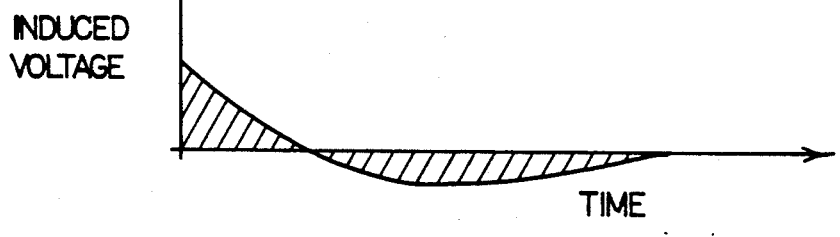
FIG. 3A
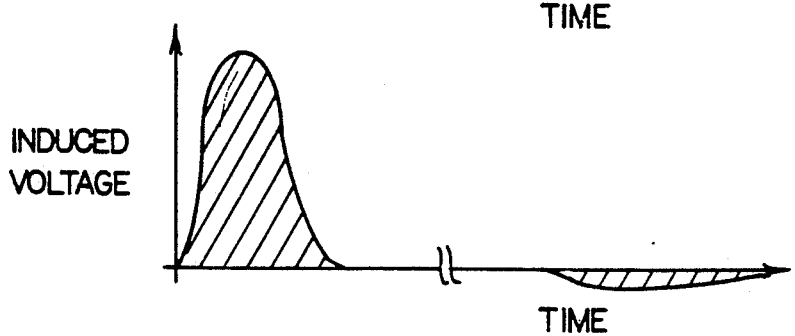
FIG. 3B

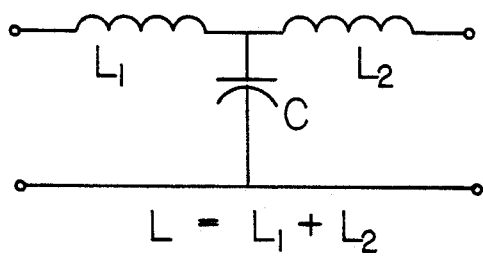
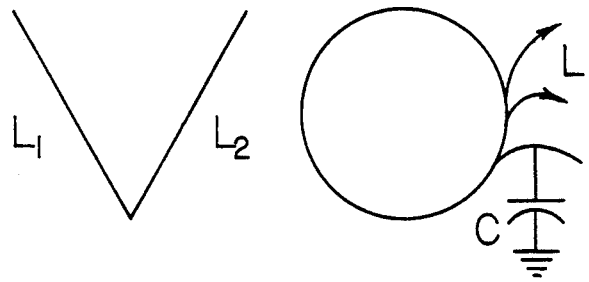
$L = L_1 + L_2$
FIG. 7A     FIG. 7B     FIG. 7C
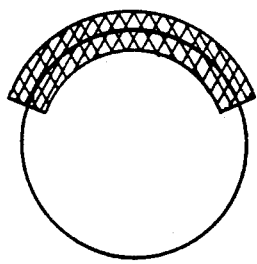
FIG. 8A     FIG. 8B
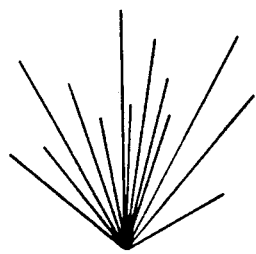
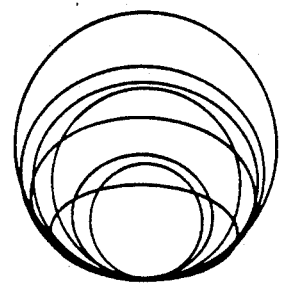
FIG. 9A     FIG. 9B
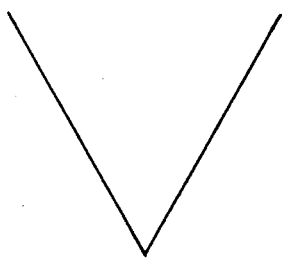
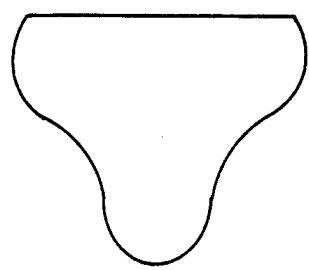
FIG. 10A     FIG. 10B

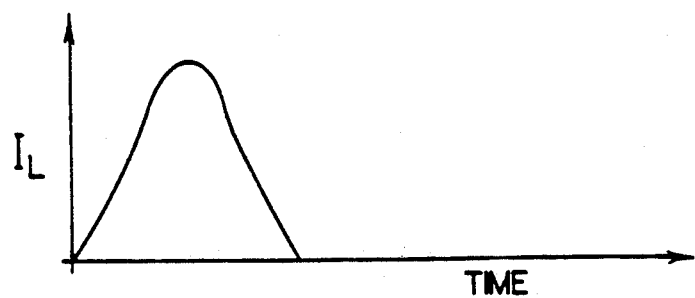
FIG. 11A
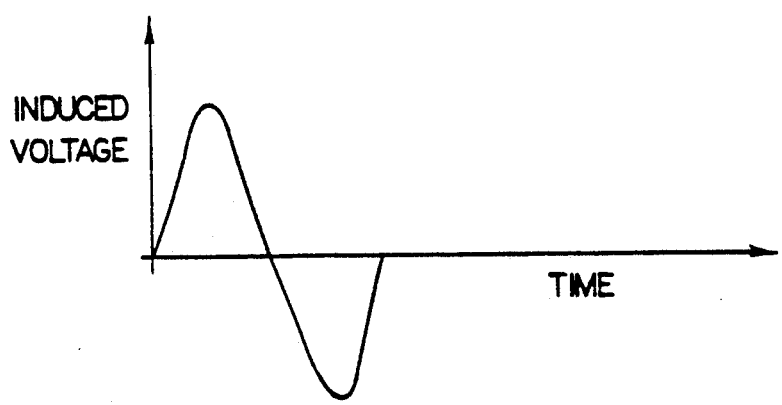
FIG. 11B
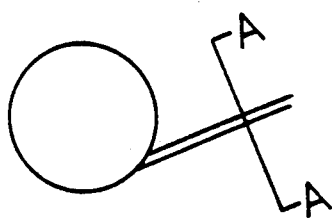
FIG. 12A          FIG. 12B          FIG. 12C
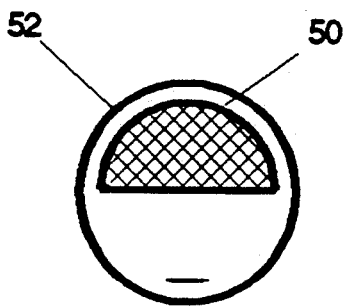
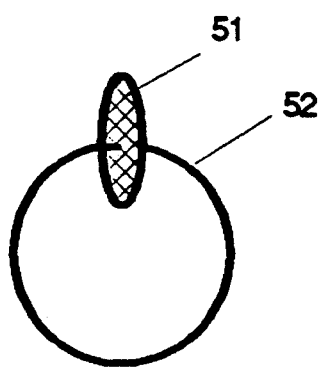
FIG. 13A          FIG. 13B

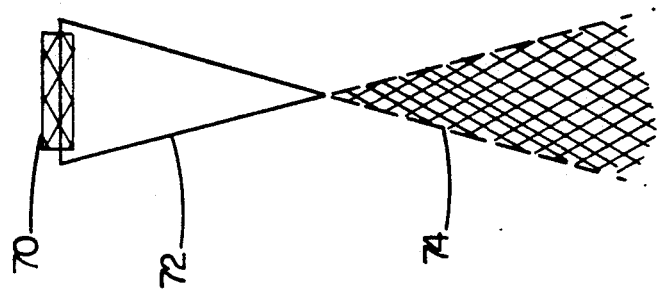
FIG 15A
FIG 15B
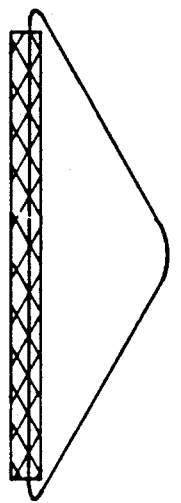
FIG 14A
FIG 14B

MAGNETIC STIMULATION DEVICE

This invention was made with Government support under a Research Grant from the National Science Foundation (Grant Number ISI-9060593).

BACKGROUND OF THE INVENTION

This invention relates to devices used to couple electrical signals into living tissue and especially to those devices which utilize magnetic stimulation to induce a current in human or animal nerve tissue.

The use of magnetic stimulation in clinical neurophysiology has been shown to be a useful research and diagnostic tool in medicine. In recent years medical researchers have found that it is possible to stimulate selected nerves with magnetically induced signals from coils carrying high current pulses. This stimulation means was found to be safe, painless, non-invasive, and easy to administer. The alternatives to magnetic stimulation are to use needle electrodes to penetrate the skin, or surface electrodes on the skin to apply high-voltage shocks through the body. Until the design of the device described herein, the main disadvantage of magnetic nerve stimulation was its imprecision.

Present magnetic stimulator coils are neither capable of precise application of stimulus nor usually oriented for proper stimulus of nerves. The most popular design uses circular coils, which are typically applied flat on the skin for stimulating the nerves. This results in an imprecise, broad stimulus which is not sufficient for accurate nerve measurements such as nerve latency. Use of existing coils results in imprecise knowledge of where primary stimulus signal is being applied, and signals which contaminate readings by stimulating adjacent tissue.

Present magnetic stimulus waveform generators, likewise, are not capable of inducing broad monopolar or symmetric bipolar signals. The current methods to generate the high current pulses for nerve stimulation usually consist of discharging a capacitor through a coil, in a short burst through a switch. FIG. 1 illustrates a typical prior art circuit. This circuit generates a bipolar current waveform in the coil (inductor) if the L-C circuit is underdamped, and a bipolar induced waveform in the nerve. Even when a critically damped or slightly overdamped waveform is used, a bipolar induced signal results. This occurs because the induced signal is the first derivative of the current waveform in the coil. FIGS. 2A and 2B illustrate a critically damped current pulse and its resultant induced voltage.

What is needed is a magnetic stimulator device designed to improve the knowledge of where the stimulus is being applied, improve the signal intensity for a given coil inductance, reduce the volume of tissue receiving the strongest stimulus signals, and reduce the contaminating affects of unwanted signals. Also needed are magnetic stimulation devices and methods for providing single polarity, precise duration, precise magnitude, induced signals for improving nerve conduction measurement.

With these improvements the technology of magnetic stimulation of body parts will be made much more exact and be able to compete with the non-magnetic techniques in stimulus accuracy, while retaining all the inherent advantages of magnetic stimulation.

SUMMARY OF THE INVENTION

The present invention provides a magnetic stimulation device for inducing electrical pulses in human or animal nerve tissue. A high power electrical current source provides specially defined current pulses to a magnetic coil which produces non-uniform magnetic fields which are concentrated at a location near one position on the coil and reduced at locations near other positions on the coil. In a preferred embodiment of the present invention a variable resistance switch is used to control the shape of the induced pulses.

BRIEF DESCRIPTION OF THE DRAWINGS

FIG. 1 is a prior art circuit diagram.

FIG. 2 is a typical prior art pulse.

FIG. 3 is a typical pulse produced by the present invention.

FIGS. 7A, B, and C demonstrate another coil design of the present invention.

FIGS. 8A and B are views of another coil design of the present invention.

FIGS. 9A and B are views of another coil design of the present invention.

FIGS. 10A and B are views of another coil design of the present invention.

FIGS. 11A and B demonstrate a symmetric bipolar induced signal.

FIGS. 12A, B, and C demonstrate another coil design of the present invention.

FIGS. 13A and B are views of coil designs using a conductive ring or coil.

FIGS. 14A and B demonstrate another coil design of the present invention.

FIGS. 15A and B demonstrate another coil design of the present invention.

DETAILED DESCRIPTION OF PREFERRED EMBODIMENT

Figure 4:
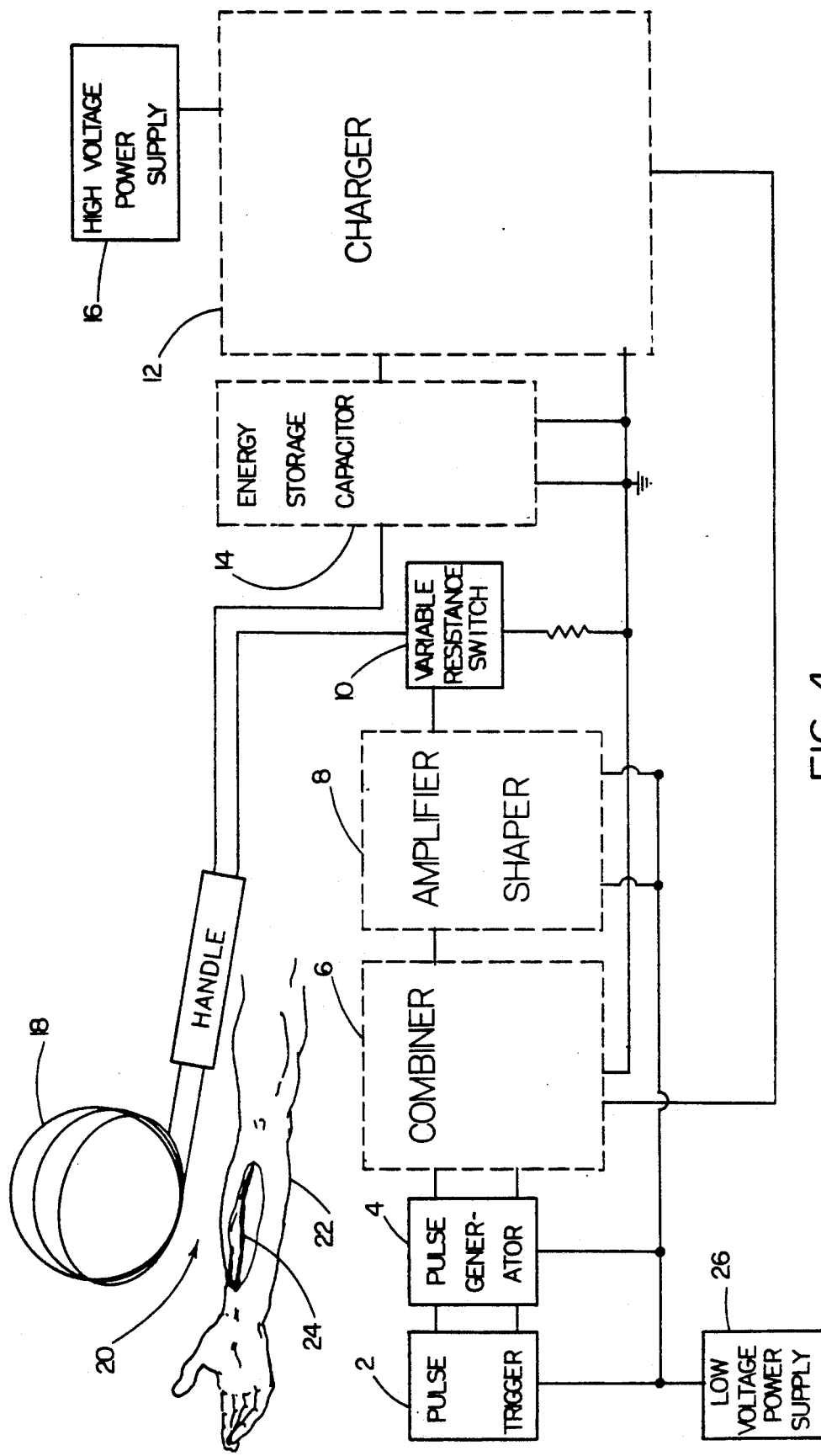
FIG. 4 is a block diagram of one embodiment of the present invention.

FIG. 3A illustrates a preferred waveshape of the electrical current flow through a stimulator coil 18 such as shown in FIG. 4 desired for measuring nerve characteristics. FIG. 3A shows the current rise through the stimulator coil 18, and the resulting induced signal is shown in FIG. 3B. The current is not permitted to decay appreciably for a period of time so as to prevent significant negative-going signals in the induced waveform for a time following the stimulator pulse. When it is allowed to decrease, it does so slowly to create a minimal negative going transient pulse.

GENERAL DESCRIPTION

Figure 5A:
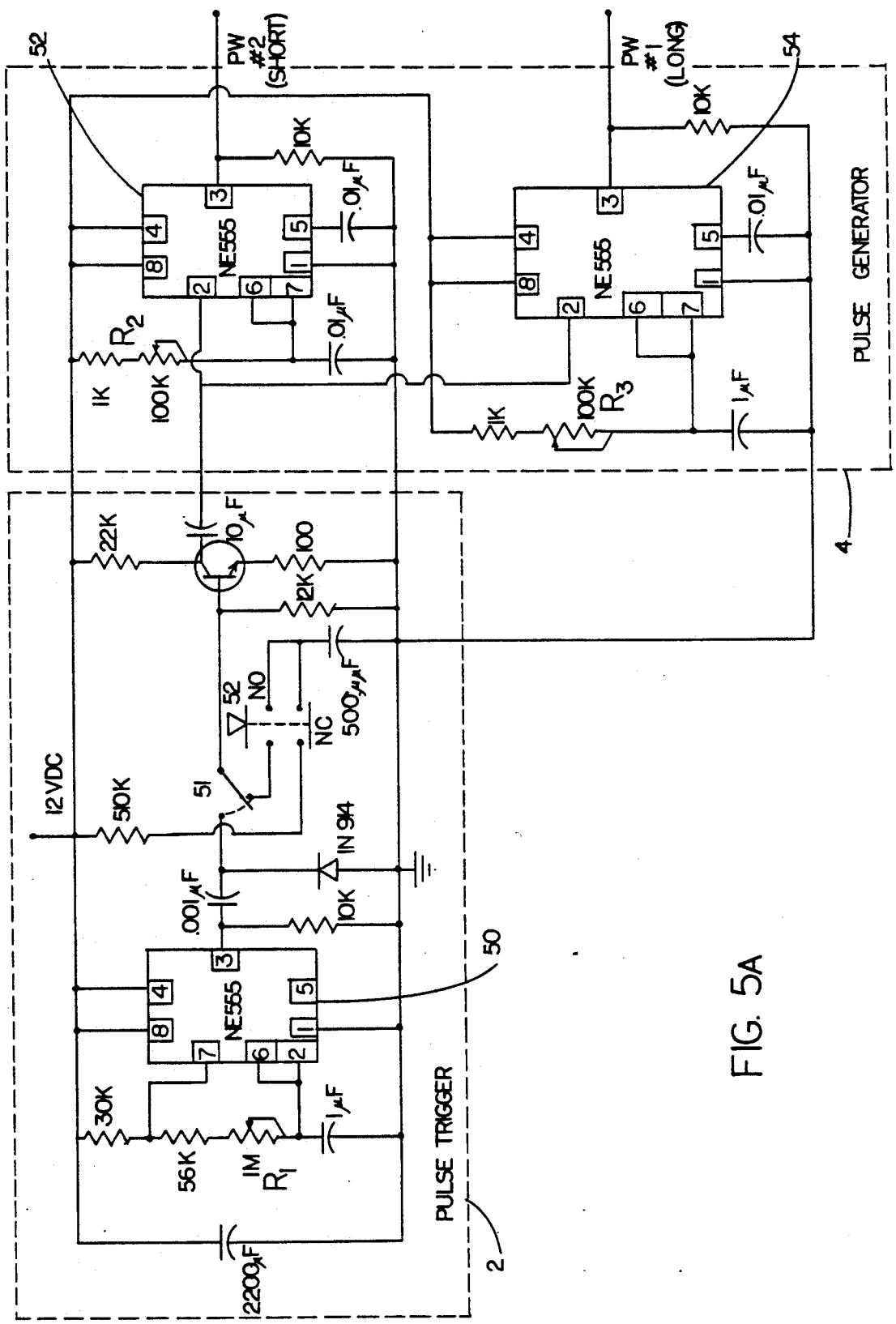
FIGS. 5A and B are electrical schematics of an embodiment of the present invention.
Figure 5B:
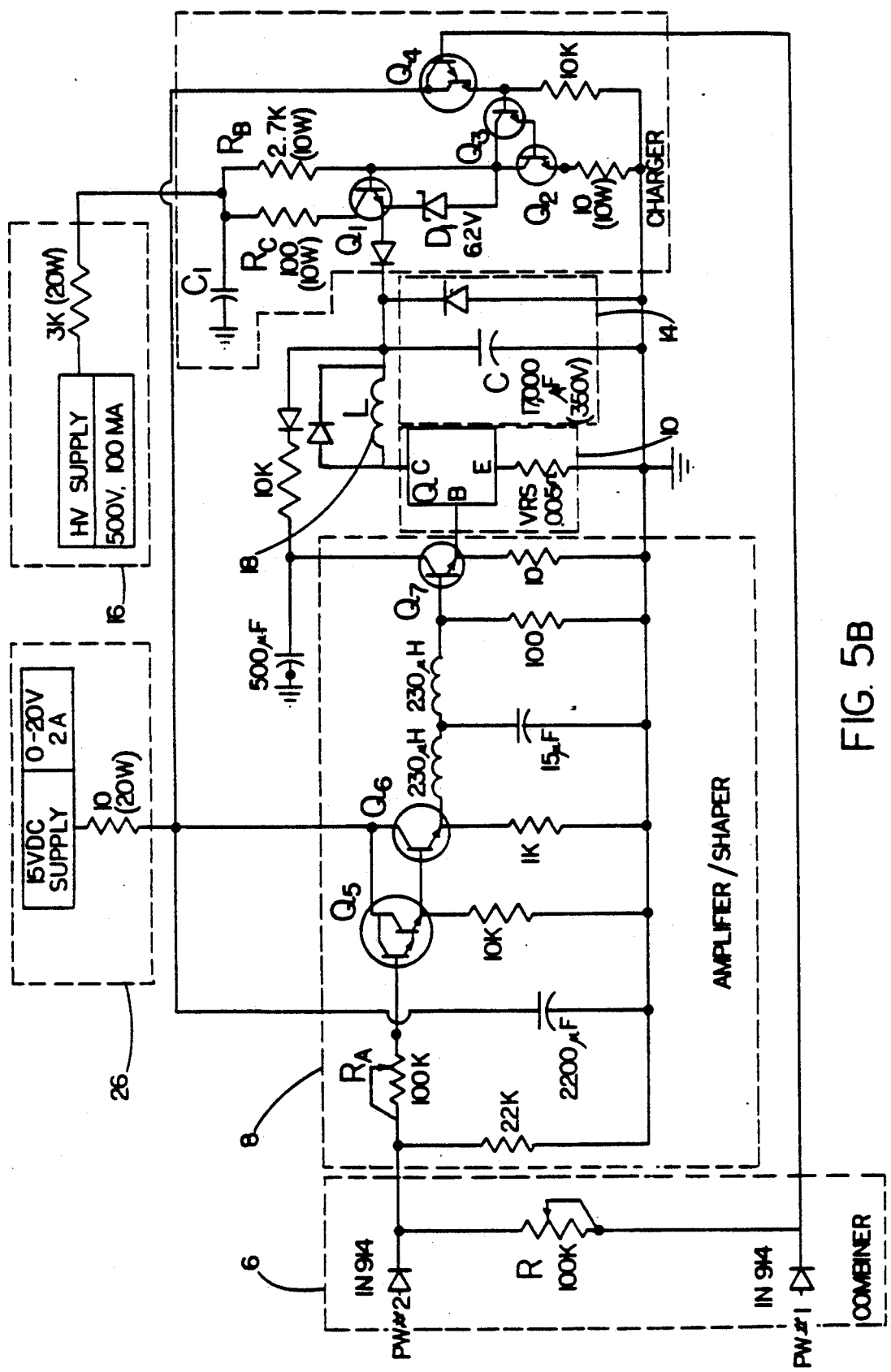

FIG. 4 illustrates a prototype embodiment of the present invention which I built in order to demonstrate the principals of the present invention. FIGS. 5A and 5B are schematic representations of the actual components used in the prototype. It was assembled with parts at hand, or locally purchased parts, and does not represent a preferred commercial design, but rather a tested embodiment which has produced the results described. The reader should understand that this is a prototype and that other embodiments will be preferred for actual use in medical practice. For example, with this prototype unit I can only generate pulses of about 1000 amperes of current through the coil about every 3 minutes, whereas in the commercial design described below, I would be able to generate many thousands of amperes of current at rates up to 10 pulses per second.

FIG. 4 illustrates a pulse trigger 2, triggering pulse generator 4, whose pulses, a short duration pulse and a longer duration pulse, are combined in a combiner 6 and also sent to a capacitor charger 12. The output of combiner 6 is amplified and shaped in amplifier/shaper 8. The longer duration pulse signal from pulse generator 4 is used to stop the charging of energy storage capacitor 14. The signal from the amplifier/shaper 8 initiated by the combined short and long duration pulses energizes a variable resistance switch 10 which is used to discharge energy storage capacitor 14 through the stimulator coil 18. Capacitor 14 has sufficient capacity to provide the current rise through the coil 18, and sustain it for a period of time. After a period of time, capacitor 14 is slowly discharged through coil 18 and variable resistance switch 10 at a programmed rate to near zero voltage. When the longer duration pulse from pulse generator 4 releases charger 12, it then recharges the capacitor 14 from a high voltage source 16 to prepare for the next stimulator pulse.

The pulse trigger 2 can generate a single trigger pulse, or can be set to automatically generate a range of repetitive trigger pulses. The pulse generators in pulse generator 4 begin generation of their pulses upon receipt of the trigger pulse. They can generate a range of different pulse widths chosen by the operator of the equipment.

At intervals determined by pulse trigger 2, switch 10 permits a very high current (in the range of one thousand Amperes in my prototype and up to ten thousand Amperes for a duration of tenths of milliseconds in the commercial unit) to flow through coil 18. This pulse of current produces a rapidly changing magnetic flux in the vicinity of coil 18. Coil 18 is shaped to produce a narrow concentrated flux pattern at a location indicated by arrow 20. In FIG. 4 the coil is shown placed above a patients arm so as to induce a voltage signal in the patients median nerve 24.

DETAILED DESCRIPTION OF SUBSYSTEMS

Pulse Trigger

In this prototype embodiment, I use an astable multivibrator 50 (NE555 integrated circuit) as building block for pulse trigger 2 to give repetitive pulses. These pulses are then differentiated, and the positive spikes are used as pulse triggers when in automatic mode. For single pulses a DPDT pushbutton switch was used to charge (NC POSITION) and discharge (NO POSITION) a 500 micro-micro Farad capacitor into approximately a 5,000 ohm load. A SPDT switch is used to select either automatic or one-shot triggers. The astable multivibrator provides pulses at rates adjustable from every 0.1 second to every 1.24 seconds. The electrical components of pulse trigger 2 are shown in FIG. 5A.

Pulse Generator

My pulse generator 4 contains two monostable multivibrators 52 and 54. These are simultaneously turned on by the pulse trigger circuit. (These were also built around NE555 integrated circuits.) One monostable multivibrator provides output pulse widths adjustable from 14 microseconds to 1 milliseconds. The other monostable multivibrator provides output pulse widths adjustable from 1 millisecond to 1 second. The output pulses are positive going pulses of approximately 12 volts peak amplitude.

A 12 Volt DC low voltage power supply 26 is used to energize both the trigger and pulse generator circuits.

Combiner

Combiner 6 is used to adjust the weights of the two pulses from the pulse generator 4. The long pulse, PW#1, (approximately 1 millisecond to 1 second duration) is sent both directly to the charger circuit (to shut-off the charging circuit) and also through resistor $R_m$. Resistor $R_m$ is used to attenuate the amplitude of the long pulse before being combined with the short pulse, PW#2, at resistor $R_a$. Resistor $R_a$ is used to adjust the amplitude of the combined signals before they enter the amplifier/shaper circuit 8. Resistor $R_a$ will determine the strength of the drive signal to variable resistor switch 10. Other amplitude controls, such as varying the high voltage supply voltage can also be used to vary signal amplitude.

Amplifier/Shaper

The amplifier/shaper 8 is shown in FIG. 5B. This circuit is used to shape the drive signal to the variable resistance switch 10, and also to provide suitable amplification. In this prototype embodiment, a cascade series of amplifiers was used to provide high impedance input and low impedance output. This is followed by a low-pass filter circuit as shown in the figure, which smooths the drive waveform and to prevent strong high-frequency components from raising the inductive reactance of the stimulator coil when switching occurs. The low-pass filter has a breakpoint of approximately 2 Khz, to correspond to the desired induced pulse width. The low-pass filter is followed by a drive amplifier used to provide a suitable drive signal to variable resistance switch 10.

Charger

The charging circuit 12 also shown in 5B. is used to charge the energy storage capacitor 14, and to prevent its charging during the period of pulse generation. During charging, resistor $R_B$ biases transistor $Q_1$ ON. Resistor $R_C$ limits current flow through transistor $Q_1$. Capacitor $C_1$ is used to speed recharging time, and reduce instantaneous loads on the high voltage power supply 16. $C_1$ should have a value several times higher than the energy storage capacitor 14. With a value of 0.02 Farads for 14, for example, $C_1$ might be 0.1 Farads. In my prototype circuit, however, a large value of capacitance was not available for $C_1$, and so available capacitance values were used, or sometimes no capacitance.

When pulses are to be generated, the longer pulse signal enters a buffer amplifier, and turns ON transistor $Q_2$. This essentially pulls the base of transistor $Q_1$ to GROUND, turning it OFF and preventing charging. Zener diode $D_2$ is used to protect transistor $Q_1$ from $V_{EBO}$ breakdown. When the pulse is removed from the buffer amplifier, transistor $Q_2$ shuts OFF, permitting $Q_1$ to again commence charging of energy storage capacitor 14. $Q_1$, $R_C$, and $D_1$ could all be removed and the charger would still work, though less efficiently.

Energy Storage Capacitor

Energy storage capacitor 14 shown in FIG. 5B supplies the energy used for generating the high-current pulse through stimulator coil 18, when the variable resistance switch 10 is turned ON. Capacitor 14 should have sufficient capacity to sustain maximum current flow through the stimulator coil 18 for a period of time after the induced pulse has been developed. In my prototype embodiment a 17,000 microFarad capacitor with a working voltage of 350 volts is used. A diode is connected across energy storage capacitor 14 to protect the capacitor against negative spikes (three diodes in parallel were used in the prototype).

Stimulator Coil

The stimulator coil 18 is used to deliver the stimulation pulses to the tissue. It is wound of highly conductive material (e.g., copper wire) with a number of turns required to achieve a particular inductance. Electrically it is essentially a pure inductance (wire size of the coil is chosen to keep resistance low, and the few turns of wire used have little capacitance). The variable resistance switch 10, the inductance of the stimulator coil 18, and other fixed resistances (from the capacitor, wires, and connectors) determine rise time of the current through the coil. The shape of this current rise will determine the resultant induced pulse shape (being the mathematical derivative of the coil current).

The mean diameter of the coil 18 will affect the rate of signal decay with distance from the point of stimulus. The larger the mean diameter, the slower the field intensity decay with distance from the coil. To increase the number of coil turns for a given inductance value, and to decrease unwanted field strength away from the point of stimulus, I typically spread the upper portion of the coil, as shown in FIG. 4. Spreading the coil upper portion accomplishes the purpose of lowering the inductance and also helps to reduce the affect of stray contaminating signals. There are a variety of coil sizes and shapes which are interchangeably used for pulse stimulus, but to keep the same drive signal, they are preferably all of approximately the same inductance value. My preferred coils for my prototype unit have an inductance of about 3 microHenry. One typical coil is constructed of five turns of #22 AWG wire with a diameter of seven centimeters, and with the top portion of the coil evenly spread out over approximately 120°. This coil had a measured inductance of 2.67 microHenry (and a Q of 147).

Variable Resistance Switch

The key element in controlling the shape of the induced pulse is controlling the current through the coil 18. This is done by controlling the effective resistance of the variable resistance switch 10. A Power Darlington Module (the ETN85-050 units) from Collmer Semiconductor, Inc. (distributer for FUJI Electric) was used in this prototype embodiment. Such units are designed for connecting in parallel to provide greater current handling capability, but only one such unit was available for my prototype design. This transistor is slowly turned ON, and brought to full conduction in the time desired for the induced pulse. A high current flow is then retained for a period after the induced pulse (to keep negative-going signals away from the induced signals for a period of time (approximately ten pulse width lengths). The drive waveform then controls the transistor to reduce the current flow and continue to discharge the capacitor 14 to near zero voltage. Then it shuts OFF. This produces induced signals which are monopolar for a predetermined time period, with very small, smooth, long-duration negative-going tail signals. The shape of the pulse through coil 18 and the shape of the induced pulse in nerve 24 are shown respectively in FIGS. 3A and 3B.

Components

The transistors shown in FIGS. 5A and 5B are all commercially available. $Q_1$, $Q_2$, and $Q_3$ are 2SC1308 and $Q_4$ and $Q_5$ are TIP-120, all available from Radio Shack. $Q_6$ and $Q_7$ are 2N6259, and $Q_8$ is an ETN85-050 available from FUJI Electric. Diodes, unless otherwise noted, are Radio Shack #276-1114. The function of resistors $R_1$, $R_2$, and $R_3$ are as follows: $R_1$ sets the pulse repetition rate (PPS), $R_2$ sets the short pulse duration, and $R_3$ sets the long pulse duration. Switch $S_1$ selects single pulse or repetitive pulse train, and switch $S_2$ initiates single pulses.

Control

Amplitude of the induced pulse can be controlled through a variety of means. Varying the voltage that capacitor 14 is charged to, will influence the current rate of change, and hence the induced signal amplitude. Varying the drive signal to the variable resistance switch 10 will also vary the current rate of change through the stimulator coil 18. This drive signal essentially varies the resistance of the circuit, controlling the current flow, and hence the induced signal.

Pulse width can be controlled through the waveshape of the drive signal to the variable resistance switch 10, or through the selection of coil characteristics.

Pulse repetition rate of the pulses can be controlled by the signal from pulse trigger 2.

Pulse shape can be controlled through selection of coil 18 and capacitor values 14, and through the waveshape of the drive signal to the variable resistance switch 10. The amplifier/shaper 8 is used to create this waveshape. FIGS. 3A and 3B illustrate the generation of monopolar induced pulses. With this signal I have produced negative excursions of about one hundred times smaller in the negative direction than in the positive direction, (e.g., 1 volt positive peak, 0.01 volt negative peak) for an essentially monopolar signal. The device, however, can also generate symmetrical bipolar pulses.

To produce symmetrical bipolar induced pulses, a symmetrical current waveform is used. I produce such waveforms in the prototype by adjusting $R_m$ to its maximum value (only a single pulse essentially enters $R_a$ to go to the amplifier/shaper 6) and a pulse width of approximately 150 microseconds for the short pulse from pulse generator 4. FIG. 11A illustrates the coil current waveform produced, and FIG. 11B illustrates the resulting induced, bipolar signal.

The accuracy of pulse stimulation location is determined by the lower radius of the stimulator coil 18, and the distance from the stimulating point of the coil 20 to the tissue or nerve to be stimulated 24.

The depth of signal penetration is a function of the coil mean diameter. The larger the coil diameter, the slower the signal decay. For deep penetration, larger coil diameters are used, and for very accurate close-by stimulation, smaller diameters are better.

Commercial Model

A commercial model of the Magnetic Stimulator Device is planned for use in Neurophysiological diagnostics. My preferred embodiment uses Insulated Gate Bipolar Transistor (IGBT) Modules for the variable resistance switch 10, and will be human-engineered for use by medical personnel. This system will include a variety of interchangeable stimulator coils for different applications. Included in its planned features will be the following elements:

A. Pulse Trigger Selector—This permits selection of three means of initiating the stimulus pulse. One is via connection to an "external" trigger source. This could be used to supply a single pulse from a remote switch such as a foot activated switch, or a repetitive pulse train from a pulse generator. Another selection is through an "automatic" setting which enables an internal selection of repetitive pulses by activating a pulse rate selector. The third means is the "manual" mode. Selection of the manual mode enables a single pulse to be generated when a single pulse pushbutton (which may be located on the stimulator coil holder) is depressed.

B. Pulse Rate Selector—This selector permits the selection of repetitive pulse rates from 1 to 10 pulses-per-second (PPS).

C. Single Pulse Pushbutton—This pushbutton, which may be located on the handle of the stimulator coil, permits a single pulse to be generated.

D. Pulse Power Selector—This selector permits selection of the power level of the output power pulse.

E. Pulse Power Indicator—This meter provides an indication of the power level available for pulsing. It monitors the charge on the power capacitor bank.

F. Cable to Stimulator Coil—This cable provides the high current pulse to the stimulator coil.

G. Cable to Meas./Record. Equip.—This cable provides information to the measuring, monitoring and recording equipments. It will provide such information as: synchronism with the stimulator pulse, power level, and current pulse waveform.

H. Pulse Stimulator Coil—A number of interchangeable coils are employed. These have approximately the same inductance value, but different characteristics according to their application. Such differences would include coil diameter differences, shape differences, and shielding differences.

I. Stimulator Coil Holder—This holder accepts the various stimulator coils. It is hand-held by the individual administering the stimulation. He has a pushbutton on the handle to activate a single pulse if desired.

The Pulse

Pulse Width

Neurophysiological studies indicate that time-constants in human nerves are such as to cause energy pulses of less than tenths of milliseconds duration to be greatly attenuated. Essentially, the research implies that recommended values of pulse duration for stimulating pulses should be of duration of 100 microseconds to 1 millisecond. Preferred embodiments of this invention, therefore, would produce pulses of such duration. The technology discussed, however, could produce a wide variety of pulse widths.

Pulse Amplitude

The magnetic field rate-of-change required to achieve the threshold of sensation for magnetically induced signals into a human forearm has been found to be on the order of a few thousand Tesla/second for pulse widths discussed above. To achieve supramaximal stimulation (usually used in nerve conduction study) tens of thousands of Tesla/second are required. These values dictate the need for peak current amplitudes through the stimulator coil 18 on the order of thousands of amperes. The preferred embodiment is thus capable of delivering peak current amplitudes of these values. It is also necessary to have control over the magnitude of the stimulation pulse for various applications, as was discussed under the control heading.

Pulse Rate

Pulses can be delivered either as single pulses in response to a trigger, or automatically at a repetitive rate. Repetitive signals permit multiple data records to be correlated for better readings. Because nerve speeds and relaxation time constants affect the rate of repeating the stimulation, it has been found that pulse repetition rates of about one to ten pulses-per-second are desired for most repetitive tests.

Pulse Shape

Unlike previous attempts at magnetic nerve stimulation, the device described in this disclosure can produce induced pulses which are either symmetrically bi-polar, monopolar (for selected time periods), or with a positive to negative amplitude ratio of greater than 10. Such pulses provide medical personnel with stimulation signals which can be accurately correlated with electromyograph signals to assess nerve conduction characteristics.

To produce the monopolar induced pulses in the preferred embodiment, the current waveform of FIG. 3A are used, resulting in an induced pulse as shown in FIG. 3B. This same signal has been shown to be capable of producing negative excursions of about one hundred times smaller in the negative direction than in the positive direction, for an essentially monopolar signal.

To produce symmetrical bipolar induced pulses, a symmetrical current waveform is used. FIG. 11A illustrates the coil current waveform produced, and FIG. 11B illustrates the resulting induced, bipolar signal.

Other Variations in Coil Design

The prototype embodiment discussed above used coil spreading of the upper portion of the coil. This spreading can begin from the point of stimulus application 20 (FIG. 4), or from any point further up from that point. The spreading can go from zero degrees to 180°, but 90° to 120° produced best results in testing. Generally best results for stimulating a linear nerve segment are achieved when the coil is in a generally perpendicular orientation and lined up with the nerve to be stimulated, as shown in FIG. 4.

A number of other embodiments of the stimulator coils can be chosen to achieve other desired signal characteristics. These embodiments can usually be combined to achieve composite results.

Figure 6D:
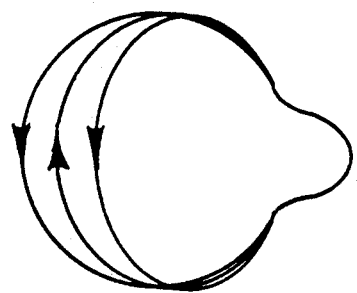
FIGS. 6A, B, C, and D are views of one coil design of the present invention.
Figure 6C:
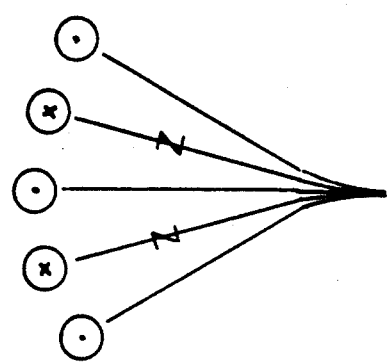
Figure 6B:
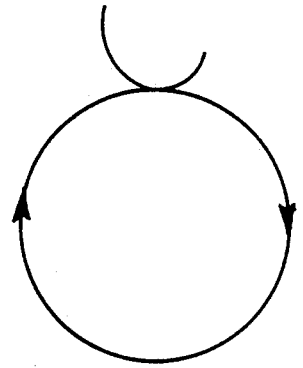
Figure 6A:
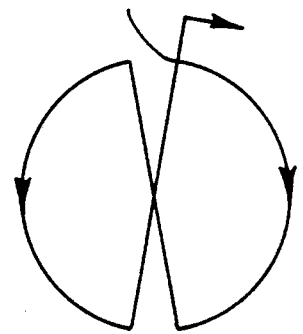

FIGS. 6A, B, C, and D show an embodiment where alternate windings are reversed in the upper part of the coil to cause the current to flow in opposite directions on adjacent turns. FIG. 6A is the reversed turn, and FIG. 6B the normal turn. FIG. 6C shows a front view of a five turn embodiment of such a coil, with the upper segment of the coil spread apart. FIG. 6D shows the same coil in side view. The lower coil segment keeps the current flowing in the same direction. This reversal in the top of the coil reduces inductive coupling.

FIGS. 7A, B, and C show an embodiment in which the stimulator coil is split with a lumped capacitor inserted between two coil segments. Any number of coil segments could be employed. By choosing an appropriate capacitance value, the coil-capacitor configuration can be made to act as a low-pass filter (with a low-frequency cutoff corresponding to the desired pulse width, e.g., 100 microseconds—10 kHz), thereby shaping the resultant induced waveform. This has advantages in reducing unwanted high frequency induced components, and also in producing a more symmetrical induced pulse.

FIGS. 8A and B show the front and side views of an embodiment in which the upper part of the coil is sheathed in a high-permeability material. A high-mu, 0.004" foil from Mu-Shield Company, Inc. in New Hampshire was used in prototype designs. This material shields the stray magnetic fields radiating from the top of the coil, reducing unwanted contaminating signals.

FIGS. 9A and B illustrate a coil comprised of upper coil spreading, and various coil diameters. Such a coil will have lower coil inductance as compared to a coil having a single diameter, and unspread coils.

FIGS. 10A and B illustrate a non-circular coil with narrow lower radius. The lower radius helps to narrow the stimulated area of tissue. The upper coil part is spread (to lower inductance) and is non-circular. The upper coil shape, because its contribution to the stimulus is negligible at close range, can be made to conform to meet the needs of other design constraints.

FIGS. 12A, B, and C illustrate the use of non-conventional conductors to construct the coils. FIG. 12A shows a typical coil, with A-A illustrating a cross-section cut across the coils. That cross-section being shown in FIG. 12B. FIG. 12B illustrates the use of small, hollow, conductive tubes to construct the coils. To reduce the effects of coil heating when used in the automatic repetitive mode, this embodiment would allow coolant flow to be circulated to remove unwanted heat. FIG. 12C illustrates the use of ribbon conductor instead of circular wire for the conductor. The use of ribbon conductors allows more turns to be used for the same inductance value, thereby increasing the effective induced power. Ribbon conductors also permit narrow cross-sections at the point of maximum stimulation.

FIGS. 13A and B illustrates the use of a conductive ring 51 or disk 50 around or inside the coil 52 to act as a secondary short circuit to the fields generated in the upper part of the coil farthest away from the point of maximum field strength. This helps to reduce the unwanted fields from this portion of the coil.

FIGS. 14A and B and FIGS. 15A and B illustrate coils designed to increase field strength contributions from vertically oriented coils by exposing much more of the positive contributing portion of the coil while shielding the negative (canceling) contributing portions of the coil. In FIGS. 15A and B the coil is exactly triangular and the top portion of the triangle is shielded by shield 70. All the exposed portion of the coil 72 contributes positively to any point below the point of the triangle designated by range 74. The coil shown in FIG. 14 is generally triangular but the points of the "triangle" have been rounded. This coil may be preferred in some cases to the one shown in FIG. 15 because it would provide better coupling to nerves located under the bottom of the coil.

Other Embodiments

A number of other embodiments of this system are possible. The pulse trigger 2 (FIG. 4) can be derived from any source that provides a short distinct signal, such as an optical-isolator switch, foot operated switch, external pulse generators, etc. The pulse generator 4 and the combiner 6 can be replaced by any system which can produce controlled pulse shapes, such as waveform synthesizers. The amplifier/shaper 8 can be any system which prepares the generated waveshape for controlling the variable resistance switch 10. The embodiment discussed in FIG. 4 used a transistor for the variable resistance switch 10, but any system or device which permits accurate control of the discharge current flow could also be used, for example insulated gate bipolar transistors, MOSFETs, switched in resistors, darlington transistors, etc. I expect to use Insulated Gate Bipolar Transistors (IGBTs) Modules, in parallel, in my first commercial product.

Another embodiment envisioned for the system would use a variable current source to control current flow through the stimulator coil 18. This system would use the pulse trigger 2 to directly trigger a waveform generator. The waveform generator would directly control the current source, which would have the stimulator coil 18 as its load impedance. This could also produce the desired nerve stimulator waveforms as shown in FIGS. 3A and B, and 11A and B.

While the above description contains many specificities, the reader should not construe these as limitations, but merely as amplifications of the preferred embodiments thereof. Those skilled in the art will envision many other possible variations within its scope. Accordingly, the reader is requested to determine the scope of the invention by the appended claims and their legal equivalents and not by the examples which have been given.

I claim:

1. A magnetic stimulation device for generating electrical pulses in human or animal tissue comprising:
    a. a high power electrical current source means for delivering current pulses in excess of 1000 amperes,
    b. a concentrating magnetic coil means for producing a non-uniform magnetic field which is concentrated at a location near at least one position (defining a high field position) on said coil means and reduced magnetic fields at locations near other positions on said coil means,
    c. a switch means connected to said source means and said coil means for permitting high current to flow in pulses through said coil means in order to generate rapidly changing magnetic fields at said high field position, and
    d. a pulse shape control means for controlling the shape of said pulses to induce essentially monopolar electrical pulses in said human or animal tissues.

2. A device as in claim 1 wherein said high power source means comprises an energy storage capacitor.

3. A device as in claim 2 wherein said switch means comprises a variable resistance switch.

4. A device as in claim 3 wherein said variable resistance switch comprises a semiconductor module.

5. A device as in claim 1 wherein said coil means comprises a coil of electrically conducting wire of at least 2 loops wherein said loops are essentially adjacent to each other at one position on the coil defining an adjacent position and substantially separated from each other at another position on the coil.

6. A device as in claim 5 wherein said separation is at least 30 degrees as measured from the center of said adjacent position.

7. A device as in claim 1 wherein said coil means comprises a coil of 2 or more loops of hollow conductive tubing.

8. A device as in claim 1 wherein said coil means comprises a coil of 2 or more loops of non-circular conductive wire.

9. A device as in claim 1 wherein said coil means comprises at least 2 turns each turn defining a loop having substantially different circumferences.

10. A device as in claim 9 wherein the loops of said coil means comprises at least 2 turns are essentially adjacent to each other at one position on said coil means and substantially separated from each other at another position on said coil means.

11. A device as in claim 1 wherein said coil means comprise a plurality of loops which are non-circular.

12. A device as in claim 1 wherein said coil means comprises a coil comprised of a plurality of turns of conductive material and further comprises a cover of high permeability material sheathing a portion of said coil.

13. A device as in claim 12 wherein the shape of said coil is triangular defining three corners.

14. A device as in claim 13 wherein at least one of said corners is rounded.

15. A device as in claim 1 wherein said coil means comprises one or more capacitors connected between one or more turns of said coil means for the purpose of shaping current flow through said coil means.

16. A device as in claim 1 wherein said coil means comprises one or more coil turns which are twisted to create a current flow in a direction opposite to the current flow of normal coil turns in a portion of said coil means away from the point of said high field position.

17. A device as in claim 1 wherein said coil means comprises a conductive ring or disk within a portion of the said coil means which is at a substantial distance from said high field position.

18. A device as in claim 1 wherein the pulse durations of said monopolar pulses are in the range of about 1 microsecond to 1 millisecond.

19. A device as in claim 1 and further comprising a pulse control means for permitting an operator to select simple pulse operation or repetitive pulse operation.

20. A device as in claim 1 wherein said coil means comprises a plurality of conductor loops having a small radius of curvature at the high field position and a larger radius of curvature at other positions of the coil means.

21. A magnetic stimulation device for generating electrical pulses in human or animal tissue comprising:
  a. a high power electrical current source means for delivering current pulses in excess of 1000 amperes,
  b. a concentrating magnetic coil means for producing a non-uniform magnetic field which is concentrated at a location near at least one position (defining a high field position) on said coil means and reduced magnetic fields at locations near other positions on said coil means,
  c. a switch means connected to said source means and said coil means for permitting high current to flow in pulses through said coil means in order to generate rapidly changing magnetic fields at said high field position, and
  d. a pulse shape control means for controlling the shape of said pulses to induce essentially symmetrical bipolar electrical pulses in said human or animal tissues.

22. A device as in claim 21 wherein the pulse durations of said symmetrical bipolar pulses are in the range of about 1 microsecond to 1 millisecond.

* * * * *